United States Patent
Petrak et al.

(10) Patent No.: US 11,666,626 B2
(45) Date of Patent: Jun. 6, 2023

(54) ANTIMICROBIAL ARTICLES PRODUCED BY ADDITIVE MANUFACTURING

(71) Applicant: ORTHOPAEDIC INNOVATION CENTRE INC., Winnipeg (CA)

(72) Inventors: Martin Petrak, Winnipeg (CA); Luke M. B. Rodgers, Chaska, MN (US)

(73) Assignee: ORTHOPAEDIC INNOVATION CENTRE INC., Winnipeg (CA)

(*) Notice: Subject to any disclaimer, the term of this patent is extended or adjusted under 35 U.S.C. 154(b) by 352 days.

(21) Appl. No.: 17/132,900

(22) Filed: Dec. 23, 2020

(65) Prior Publication Data

US 2021/0113651 A1 Apr. 22, 2021

Related U.S. Application Data

(62) Division of application No. 14/441,637, filed as application No. PCT/CA2013/050871 on Nov. 14, 2013, now Pat. No. 10,905,740.

(60) Provisional application No. 61/895,130, filed on Oct. 24, 2013, provisional application No. 61/726,433, filed on Nov. 14, 2012.

(51) Int. Cl.

| | |
|---|---|
| *A61K 38/14* | (2006.01) |
| *B33Y 70/00* | (2020.01) |
| *B29C 48/00* | (2019.01) |
| *A61L 27/54* | (2006.01) |
| *A61K 47/34* | (2017.01) |
| *A61K 31/7036* | (2006.01) |
| *A61L 27/18* | (2006.01) |
| *A61L 27/34* | (2006.01) |
| *A61M 5/142* | (2006.01) |
| *A61K 45/06* | (2006.01) |
| *A61K 31/7048* | (2006.01) |
| *A61L 15/26* | (2006.01) |
| *A61L 15/46* | (2006.01) |
| *A61K 9/00* | (2006.01) |
| *A61L 15/44* | (2006.01) |
| *A61L 31/16* | (2006.01) |
| *A61L 31/10* | (2006.01) |
| *A61L 31/06* | (2006.01) |
| *A61N 1/375* | (2006.01) |
| *B33Y 80/00* | (2015.01) |
| *A61K 47/32* | (2006.01) |
| *A61L 27/16* | (2006.01) |
| *A61C 19/06* | (2006.01) |
| *B29L 31/00* | (2006.01) |
| *A61C 8/00* | (2006.01) |
| *B33Y 10/00* | (2015.01) |

(52) U.S. Cl.
CPC ............ *A61K 38/14* (2013.01); *A61K 9/0024* (2013.01); *A61K 31/7036* (2013.01); *A61K 31/7048* (2013.01); *A61K 45/06* (2013.01); *A61K 47/32* (2013.01); *A61K 47/34* (2013.01); *A61L 15/26* (2013.01); *A61L 15/44* (2013.01); *A61L 15/46* (2013.01); *A61L 27/16* (2013.01); *A61L 27/18* (2013.01); *A61L 27/34* (2013.01); *A61L 27/54* (2013.01); *A61L 31/06* (2013.01); *A61L 31/10* (2013.01); *A61L 31/16* (2013.01); *A61M 5/142* (2013.01); *A61M 5/14276* (2013.01); *A61N 1/375* (2013.01); *A61N 1/37512* (2017.08); *B29C 48/022* (2019.02); *B33Y 70/00* (2014.12); *B33Y 80/00* (2014.12); *A61C 8/00* (2013.01); *A61C 19/06* (2013.01); *A61L 2300/102* (2013.01); *A61L 2300/104* (2013.01); *A61L 2300/23* (2013.01); *A61L 2300/252* (2013.01); *A61L 2300/406* (2013.01); *A61L 2300/412* (2013.01); *A61L 2300/414* (2013.01); *A61L 2430/02* (2013.01); *A61L 2430/12* (2013.01); *A61M 2205/0205* (2013.01); *A61M 2205/04* (2013.01); *B29L 2031/753* (2013.01); *B29L 2031/7532* (2013.01); *B33Y 10/00* (2014.12)

(58) Field of Classification Search
None
See application file for complete search history.

*Primary Examiner* — Robert A Wax
*Assistant Examiner* — Randeep Singh
(74) *Attorney, Agent, or Firm* — Gowling WLG (Canada) LLP

(57) ABSTRACT

An antibiotic-eluting article for implantation into a mammalian subject, produced by an additive manufacturing process wherein a polymeric material is concurrently deposited with a selected antibiotic. The additive manufacturing process is a fused deposition modeling process. The antibiotic-eluting article may be temporary or permanent orthopaedic skeletal component, an orthopaedic articulating joint replacement component, and/or an external hard-shell casing for an implantable device. One or more bone-growth-promoting compositions may be concurrently deposited with the polymeric material. The implantable device may be a cardiac pacemaker, a spinal cord stimulator, a neurostimulation system, an intrathecal drug pump for delivery of medicants into the spinal fluid, and infusion pump for delivery of chemotherapeutics and or anti-spasmodics, an insulin pump, an osmotic pump, and a heparin pump.

16 Claims, No Drawings

ANTIMICROBIAL ARTICLES PRODUCED BY ADDITIVE MANUFACTURING

CROSS-REFERENCE TO RELATED APPLICATIONS

This application is a division of application Ser. No. 14/441,637 filed on May 8, 2015, filed as Application Number PCT/CA2013/050871 on May 8, 2015, Provisional Application No. 61/895,130 filed on Oct. 24, 2013, Provisional Application No. 61/726,433 filed on Nov. 14, 2012.

TECHNICAL FIELD

Various embodiments disclosed herein generally relate to implantable medical devices. More specifically, this disclosure pertains to implantable medical devices provided with antimicrobial properties throughout their structures and on their surfaces.

BACKGROUND

Numerous types of medical devices have been developed for implantation into patients' bodies. For example, it has become common practice for dentists to provide their patients with custom dental prosthesis and or implants to replace non-functional or missing teeth. The replacement prosthesis and or implants can be individually designed and manufactured for precise installation into specific pre-identified sites. It has become routine for patients with abnormal or irregular rates of heart contractions, to have pacemaker devices installed under their skin in the chest area or alternatively, in their abdomens. Patients with debilitating degenerative diseases affecting their joints and or skeletal elements are now able to have a large measure of their quality of life restored by replacement of the afflicted structures with man-made artificial implants such as replacement hip components, knee joint components, shoulder components, and the like. Patients who've suffered extreme trauma resulting in severely fractured bones are often provided with fracture fixation plates, fixtures, pins, nails, intramedullary rods, and the like to hold fractured bone segments together during the healing process and/or to replace destroyed or missing skeletal segments. However, all of these types of implantable devices expose the patients to risk of post-installation infection along and/or about the outer surfaces of the devices serving as colonization sites. Particularly problematic is the establishment of infectious biofilms on the surfaces of implanted devices. More severe cases of infection often result in microbial penetration into the inner structural components of the implants requiring their removal and replacement.

Numerous strategies have been employed in attempts to prevent post-installation infections occurring on and about the surfaces live implanted medical devices. For example, flexible resilient silicone-based coatings with antimicrobial and or anti-fungal additives have been developed for encasing the outer surfaces of medical implants at the time of implant manufacture. Such coatings are typically produced by first, dissolving a suitable silicone exemplified by methyltri-methoxy silanes, methyl tri-acetoxy silanes, tetratchlorosilanes, vinyl trimetho-ryl silanes, gamma-ureidopropyltrimethoxy silanes, and the like, in a suitable solvent exemplified by toluenes, hexanes, xylenes, tetrahydrofurans, cyclohexanones, and the like. Second, dissolving an antimicrobial compound and/or an anti-fungal compound in a suitable solvent exemplified by n-methylpyrrolidinone, alkylesters of $C_{1-12}$ carboxylic acids, and the like. Third, mixing together the silane solution and the antimicrobial and or anti-fungal solution. Four, immersing medical implants into the mixed solutions followed by removal and air-drying of the encased implants, then baking at about 9° C. for up to one hour to set the coaling and to completely evaporate the solvents. Such antibiotic-encased implants are purported to release the antimicrobial and/or anti-fungal compounds upon contact of the medical implant with tissues after implantation.

Another common approach has been to incorporate antimicrobial compounds and or drugs into implants comprising polymeric materials, during their manufacture so that the antimicrobial compounds are eluted from the implants into the surrounding. These types of implants are generally referred to as drug-eluting implants. Some such implants are manufactured by dissolving the antimicrobial compounds into one or more solvents used for solubilising selected polymeric materials. The solubilised polymeric materials and antimicrobial compounds are mixed together and then poured or dispensed into forms wherein they solidify, and then are finished into the final implant. Other strategies involve first preparing an implant, then producing one or more recesses and or crevices in selected locations on the outer surface, and then filling with recesses and or crevices with a drug delivery matrix that this allowed to at least semi-harden. The drugs are then eluted from the matrix over a period of time. In some implant combinations, for example a "ball" and "socket" combination for a complete hip replacement or a total knee replacement package comprising a femoral component, a tibial tray, a tibial insert, and a patellar component, the drug delivery matrix may be incorporated into weight-bearing surfaces of one or more components so that the drugs are released by frictional forces created when two or more implant components rub against each other during their normal articulating functions. Other implant drug-eluting strategies have reservoirs east into the implants' interior structure. The reservoirs are filled with drug solutions prior to installation of an implant into a patient. Some implants are configured to communicate and cooperate with external reservoirs containing drug solutions that are externally pumped into and/or about the implants on prophylactic schedules or alternatively, when an infection is detected. It is general practise to use antibiotic-loaded cements exemplified by PROSTALAC® (PROSTALAC is a registered trademark of Depuy Orthopaedic Inc., Warsaw, Ind., USA) and SIMPLEX® (SIMPLEX is a registered trademark of Howmedica Osteonics Corp., Mahwah, N.J., USA) for installation of orthopaedic implants. While these cements have considerable value for minimizing the occurrence of post-operative infections immediately after installation of orthopaedic implants, their long-term benefits are limited because the antibiotics tend to rapidly dissipate from the surfaces of the cements upon exposure to mammalian tissues.

There still remain numerous infection-susceptibility related problems with the implants commonly available and in general use. There are concerns that the efficacies of some antimicrobial compounds and/or drugs are altered or compromised by the solvents which are used for their dissolution and/or by solvents used for dissolution of polymeric materials used for casting implants. Furthermore, it is known that the efficacies of drug-eluting implants increasingly diminish over time and are limited by drug "loading" limitations by the implant manufacturing processes. Implants provided with drug-loaded recesses/crevices may provide protection from infections about the crevice sites for a period of time, but are quite susceptible to microbial colonization and biofilm formation on their surface areas at locations removed from the recesses/crevices. Compounding these problems, are the surgical challenges of removing the infected implants, abrading surrounding infected skeletal structures, excising surrounding infected tissues, and installing replacement implants.

SUMMARY

The present disclosure pertains to implantable antimicrobial medical devices having antimicrobial compounds evenly sequestered throughout their structural matrices and distributed across their surfaces. The antimicrobial compounds may be eluted from the surfaces and from within the structural matrices after implantation of the medical devices into a mammalian subject. The present disclosure also pertains to methods for producing implantable medical devices comprising datable antimicrobial compounds sequestered within their structural matrices and distributed across their surfaces.

DETAILED DESCRIPTION

The present disclosure pertains to methods for producing implantable antibiotic-eluting polymeric medical devices having antimicrobial compounds and or bactericidal compounds homogenously distributed and sequestered throughout their structural matrix and across their surfaces. The present disclosure also pertains to implantable antibiotic-sequestering and eluting medical devices produced by the exemplary methods disclosed herein.

The exemplary methods of the present disclosure are particularly useful for producing substantially rigid articles that are suitable for surgical implantation into mammalian bodies, for example humans, primates, livestock, ruminants, equines, canines, felines, and the like.

The exemplary methods are also useful for producing external hard-shell casings for implantable devices such as cardiac pacemakers, spinal cord stimulators, neurostimulation systems, intrathecal drug pumps for delivery of medicants into the spinal fluid, infusion pumps for delivery of chemotherapeutics and/or anti-spasmodics, insulin pumps, osmotic pumps, heparin pumps, and the like. The exemplary methods are also useful for producing dental prosthesis, dental implants comprising one or more replacement tooth components, and the like. The exemplary methods are also useful for producing transcutaneous skin surface treatment devices exemplified by devices for providing transcutaneous electrical nerve stimulation and by devices for providing long-term percutaneous access. The exemplary methods are also useful for producing wound treatment surface devices exemplified by staples and sutures, and the like. The exemplary methods are particularly useful for producing three-dimensional intricate orthopaedic skeletal components including but not limited to articulating joint replacements, hip joint spacers, knee joint spacers, shoulder joint spacers, and the like. The three-dimensional intricate orthopaedic skeletal components may be temporary structures or alternatively, permanent structures.

The exemplary methods generally incorporate into manufacturing processes using additive manufacturing technologies, the concurrent deposition of one or more antimicrobial and or biocidal compositions with the base feedstock materials to form the three-dimensional physical structures comprising the implantable antimicrobial articles of the present disclosure. The articles may be formed into solid and dense non-porous three-dimensional structures. Alternatively, the structures may be formed into heterogenous three-dimensional structures comprising solid regions and porous regions. Alternatively, the structures may comprise inner cores having heterogenous three-dimensional structures that are overlaid with outer coverings comprising one or more solid dense layers. One or more selected antimicrobial compositions may be incorporated into the inner cores and/or into the outer coverings. Alternatively, the structures may comprise inner cores comprising a first heterogenous three-dimensional structure with a first degree of porosity, overlaid with one or more layers of a second heterogenous three-dimensional structure with a second degree of porosity. One or more selected antibiotic compositions may be incorporated into the inner cores and or into the outer layers. If so desired, the articles can be formed having more than three zones of porosity ranging from the inner cores to the outer surfaces.

Suitable additive manufacturing technologies include molten polymer deposition exemplified by fused deposition modeling and the like; binding of granular materials exemplified by selective laser sintering, selective laser melting, selective heat sintering, election beam melting, and the like; photopolymerization of solubilised polymeric materials exemplified by digital light processing, stereolithography and the like. One or more antibiotic compositions are concurrently deposited with the polymeric materials resulting in sequestration of the antibiotic compositions within and about the matrix formed by the polymeric materials. The antibiotic compositions are deposited at rates that will provide in the articles of the present disclosure, from about 0.01% w/w to about 25% w/w of the antibiotic active ingredient by weight of the total weight of an antimicrobial article. For example, about 0.01% w/w, about 0.05% w/w, about 0.1% w/w, about 0.2% w/w, about 0.5% w/w, about 0.4% w/w, about 0.5% w/w, about 0.75% w/w, about 1.0% w/w, about 1.25% w/w, about 1.5% w/w, about 1.75% w/w, about 2.0% w/w, about 2.25% w/w, about 2.5% w/w, about 2.75% w/w, about 3.0% w/w, about 3.25% w/w, about 3.5% w/w, about 3.75% w/w, about 4.0% w/w, about 4.25% w/w, about 4.5% w/w, about 4.75% w/w, about 5.0% w/w, about 5.25% w/w, about 5.5% w/w, about 5.75% w/w, about 6.0% w/w, about 7.0% w/w, about 8.0% w/w, about 9.0% w/w, about 10.0% w/w, about 15.0% w/w, about 20.0% w/w, about 25.0% w/w, and therebetween.

The term "antimicrobial" as used herein means antibiotic, antiseptic, disinfectant. Classes of antibiotic compositions that may be useful for in the methods of the present disclosure for producing antimicrobial implantable medical devices include aminoglycosides exemplified by tobramycin, gentamicin, neomycin, streptomycin, and the like; azoles exemplified by fluconazole, itraconazole, and the like; β-lactam antibiotics exemplified by penams, cephems, carbapenems, monobactams, β-lactamase inhibitors, and the like; cephalosporins exemplified by cefacetrile, cefadroxyl, cephalexin, cefazolin, cefproxil, cefbuperazone, and the like; chloramphenicol; clindamycin; fusidic acid; glycopeptides exemplified by vancomycin, teicoplanin, ramoplanin, and the like; macrolides exemplified by azithromycin, clarithromycin, dirithromysin, erythromycin, spiramycin, tylosin, and the like; metronidazole; mupirocin; penicillins exemplified by benzylpenicillin, procaine benzylpenicillin, benzathine benzylpenicillin, phenoxymethylpenicillin, and the like; polyenes exemplified by amphotericin B, nystatin, natamycin, and the like; quinolones exemplified by ciprofloxacin, ofloxacin, danofloxacin, and the like; rifamycins exemplified by rifampicin, rifabutin, rifapentine, rifaximin, and the like; sufonamides exemplified by sulfacetamine, sulfadoxine, and the like; tetracyclines exemplified by doxycycline, minocycline, tigecycline, and the like; and trimethoprim, among others. It is expected that tobramycin and or gentamicin and/or neomycin and/or vancomycin are particularly suitable for concurrent deposition with polymeric materials for additive manufacturing of the antimicrobial medical devices of the present disclosure.

Various thermoplastic polymers and or free radical polymers and or cross-linked polymers may be used for concurrent deposition with antibiotic compositions to produce the antimicrobial articles disclosed herein. For example poly (methyl methacrylates), acrylonitrile butadiene styrenes, polycarbonates, blends of acrylonitrile butadiene styrene(s) and polycarbonate(s), polyether ether ketones, polyethylenes, polyamides, polylactic acids, polyphenylsulfones, polystyrenes, nylon particularly nylon 12, among others. Also useful are methylmethacrylates, polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, block copolymers, multi-block co-polymers, multi-block co-polymers with polyethylene glycol (PKG), polyols, terpolymers and mixtures thereof. Also useful is incorporation of glass fibres during deposition of selected polymers and antibiotic compositions.

If so desired for manufacture of the three-dimensional intricate orthopaedic skeletal components disclosed herein, it is suitable to deposit one or more bone-growth-promoting compositions concurrently with the polymeric materials and the antibiotic compositions resulting in sequestration of the antibiotic compositions and bone-growth-promoting compositions within and about the matrix formed by the polymeric materials. Suitable bone-growth-promoting compositions are exemplified by hyaluronic acid, β-TCP compositions, SOST (sclerostin) antagonists for modulating the Wnt signaling pathway, Wise antagonists for modulating the Wnt signaling pathway, LRP antagonists for modulating the Wnt signaling pathway, (3-(((4-tert-butyl-benzyl)-(pyridine-3-sulfonyl)-amino)-methyl)-phenoxy)-acetic-acid and its analogs, 7-[(4-butyl-benzyl)-methanesulfonyl-amino]-heptanoic acid and its analogs, 7-{[2-(3,5-dichloro-phenoxyl)-ethyl]-methanesulfonyl-amino}-heptanoic acid and its analogs, 3-benzothiepin derivatives, and the like.

Fused deposition modeling is an extrusion-based technology used in rapid prototyping and additive manufacturing developed by Stratasys Ltd. (Eden Prairie, Minn., USA) in the late 1980s and commercialized in systems sold by Stratasys under the registered trademark "FDM®". A plastic filament is unwound from a coil and supplied to an extrusion nozzle which turns on and off the flow of the plastic filament into and through the extrusion nozzle. The nozzle is heated to melt the material and can be moved in both horizontal and vertical directions by a numerically controlled mechanism that is directly controlled by a computer-aided manufacturing software package. The model or part is produced by extending small beads of thermoplastic material to form layers, as the material solidifies upon cooling after extrusion from the nozzle. Accordingly, one or more selected antibiotics may be incorporated into plastic filaments during preparation of the filaments, and supplied as a modeling filament for extrusion in a fused deposition modeling system. Alternatively, one or more selected antibiotics may be supplied in a powdered form or optionally, in a fluid form, to the extrusion nozzle concurrently with the filament.

Some exemplary embodiments of the present disclosure pertain to antibiotic-containing polymeric filaments prepared as FDM® modeling filaments wherein the antibiotic-containing polymeric filaments comprise a blend of one or more thermoplastic polymers and/or one or more free radical polymers and/or one or more cross-linked polymers selected from the list provided above, for example, with one or more antibiotics selected from the list provided above and or one or more bone-growth-promoting compositions selected from the list provided above. For example, the antibiotic content of an exemplary antibiotic-containing polymeric filament may comprise about 0.01% w/w, about 0.05% w/w, about 0.1% w/w, about 0.2% w/w, about 0.3% w/w, about 0.4% w/w, about 0.5% w/w, about 0.75% w/w, about 1.0% w/w, about 1.25% w/w, about 1.5% w/w, about 1.75% w/w, about 2.0% w/w, about 2.25% w/w, about 2.5% w/w, about 2.75% w/w, about 3.0% w/w, about 3.25% w/w, about 3.5% w/w, about 3.75% w/w, about 4.0% w/w, about 4.25% w/w, about 4.5% w/w, about 4.75% w/w, about 5.0% w/w, about 5.25% w/w, about 5.5% w/w, about 5.75% w/w, about 6.0% w/w, about 7.0% w/w, about 8.0% w/w, about 9.0% w/w, about 10.0% w/w, about 15.0% w/w, about 20.0% w/w, about 25.0% w/w, and therebetween. For example, the bone-growth-promoting composition content of an exemplary antibiotic-containing polymeric filament may comprise about 0.01% w/w, about 0.05% w/w, about 0.1% w/w, about 0.2% w/w, about 0.3% w/w, about 0.4% w/w, about 0.5% w/w, about 0.75% w/w, about 1.0% w/w, about 1.25% w/w, about 1.5% w/w, about 1.75% w/w, about 2.0% w/w, about 2.25% w/w, about 2.5% w/w, about 2.75% w/w, about 3.0% w/w, about 3.25% w/w, about 3.5% w/w, about 3.75% w/w, about 4.9% w/w, about 4.25% w/w, about 4.5% w/w, about 4.75% w/w, about 5.0% w/w, about 5.25% w/w, about 5.5% w/w, about 5.75% w/w, about 6.0% w/w, about 7.0% w/w, about 8.0% w/w, about 9.0% w/w, about 10.0% w/w, about 15.0% w/w, about 20.0% w/w, about 25.0% w/w, and therebetween. Some exemplary embodiments of the present disclosure pertain to antibiotic-containing core-shell polymeric filaments prepared as FDM® modeling filaments such as those disclosed in US Patent Publication Nos. 2012/0231225 A1 and 2013/0224423 A1 (both assigned to Stratasys, Inc.). An exemplary core-shell polymeric filament includes a core portion and shell portion, both extending along a longitudinal length. The core portion is the inner portion of filament located around a central axis, and the shell portion is the outer portion of the filament located adjacent to the outer surface of the filament. The core portion compositionally includes a first polymeric material, referred to as a core material. The shell portion compositionally includes a second polymeric material referred to as a shell material. The core and shell materials each include one or more base polymers and, optionally, one or more additives.

It is within the scope of the present disclosure to incorporate one or more antimicrobial compounds disclosed above into the core materials comprising core-shell polymeric filaments, alternatively into the shell materials comprising core-shell polymeric filaments, alternatively into both core materials and shell materials comprising core-shell polymeric filaments. It is also within the scope of the present disclosure to incorporate one or more bone-growth promoting compounds disclosed above into the core materials comprising core-shell polymeric filaments, alternatively into the shell materials comprising core-shell polymeric filaments, alternatively into both core materials and shell materials comprising core-shell polymeric filaments. It is also within the scope of the present disclosure to incorporate one or more antibiotic compounds and one or more bone-growth promoting compounds disclosed above into the core materials comprising core-shell polymeric filaments, alternatively into the shell materials comprising core-shell polymeric filaments, alternatively into both core materials and shill materials comprising core-shell polymeric filaments.

The antibiotic compounds and/or bone-growth-promoting compounds may be incorporated into the core material of a core-shell polymeric filament by dry-blending together a selected antibiotic with a selected polymer to produce a master blend of an antibiotic-containing core material. The antibiotic compounds and or bone-growth-promoting compounds may be incorporated into the shell material of a core-shell polymeric filament by dry-blending together a selected antibiotic with a selected polymer to produce a master blend of an antibiotic-containing shell material. A core-shell polymeric filament comprising an antibiotic and/or a bone-growth-promoting compound in its core is prepared by combining the antibiotic-containing core material with a shell material dial is absent any antibiotics or bone growth-promoting compounds. A core-shell polymeric filament comprising an antibiotic and/or a bone-growth-promoting compound in its shell is be prepared by combining the antibiotic-containing shell material with a core material that is absent any antibiotics or bone growth-promoting compounds. A core-shell polymeric filament comprising an antibiotic and/or a bone-growth-promoting compound in its core and its shell is prepared by combining the antibiotic-containing core material master blend with the antibiotic-containing shell material master blend. The master blends comprising the antibiotic compositions and/or the bone-growth-promoting compounds should have a sufficient content of the antibiotic compositions and or the bone-growth-promoting compounds to enable their deposition in the core components and the shell components of the polymeric filaments at rates that will provide in the articles of the present disclosure, from about 0.01% w/w to about 25% w/w of the antibiotic active ingredient by weight of the total weight of an antimicrobial article. For example, about 0.01% w/w, about 0.05% w/w, about 0.1% w/w, about 0.2% w/w, about 0.3% w/w, about 0.4% w/w, about 0.5% w/w, about 0.75% w/w, about 1.0% w/w, about 1.25% w/w, about 1.5% w/w, about 1.75% w/w, about 2.0% w/w, about 2.25% w/w, about 2.5% w/w, about 2.75% w/w, about 3.0% w/w, about 3.25% w/w, about 3.5% w/w, about 3.75% w/w, about 4.0% w/w, about 4.25% w/w, about 4.5% w/w, about 4.75% w/w, about 5.0% w/w, about 5.25% w/w, about 5.5% w/w, about 5.75% w/w, about 6.0% w/w, about 7.0% w/w, about 8.0% w/w, about 9.0% w/w, about 10.0% w/w, about 15.0% w/w, about 20.0% w/w, about 25.0% w/w, and therebetween.

The 3D printing methods of the present disclosure may additionally include additionally or alternatively comprise steps of concurrent deposition of a first antibiotic composition or mixture of antibiotic compositions and or a first bone-growth-promoting composition with a selected polymeric material in several layers to form the core of a three-dimensional antimicrobial article, followed by concurrent deposition of a second first antibiotic composition or mixture of antibiotic compositions and or a second bone-growth-promoting composition with the selected polymeric material to form the outer regions and surfaces of the antimicrobial article. The methods may additionally comprise concurrent deposition of additional layers of a third antibiotic composition or mixture of antibiotic compositions and/or a third bone-growth-promoting composition if so desired. It is optional to provide a final outer surface layer to which is added a biocidal composition exemplified by silver nanoparticles, zinc pyrithione, cationic polymeric biocides, and the like. It is optional to provide a final outer surface layer to which is added a bone-growth-promoting composition exemplified by hyaluronic acid, β-TCP compositions, 3-benzothiepin derivatives, and the like.

It is also optional to provide a final outer surface layer to which is added mixture of a biocidal composition and a bone-growth-promoting composition. The outer surface layer comprising the biocidal coating and or the bone-growth-promoting composition may be applied by the same additive manufacturing process used to produce the core structural matrix of the three-dimensional antimicrobial article. Alternatively, the outer surface layer may be applied as a coating over the core structural matrix of the three-dimensional antimicrobial article. The outer coating may be applied by processes exemplified by dipping, spraying, soaking, infusing, powder-coating, sputter-coating, arc depositing, and the like.

The antibiotic-eluting articles of the present disclosure are exemplified by orthopaedic skeletal components, orthopaedic articulating joint replacement components, and bone spacers. Also included are temporary orthopaedic components for short-term implantation while the permanent replacement orthopaedic components are being produced. The term "short-term" as used herein means 365 days and less. The antibiotic-eluting articles of the present disclosure are also exemplified by external hard-shell casings for implantable devices such as cardiac pacemakers, spinal cord stimulators, neurostimulation systems, intrathecal drug pumps for delivery of medicants into the spinal fluid, infusion pumps for delivery of chemotherapeutics and/or anti-spasmodics, insulin pumps, osmotic pumps, heparin pumps, and the like. The antibiotic-eluting articles of the present disclosure are also exemplified by implantable dental prosthesis, dental implants comprising one or more replacement tooth components, and the like. The antibiotic-eluting articles of the present disclosure are also exemplified by transcutaneous skin surface treatment devices for providing transcutaneous electrical nerve stimulation and by devices for providing long-term percutaneous access. The antibiotic-eluting articles of the present disclosure are also exemplified by wound treatment surface devices exemplified by staples and sutures, and the like.

EXAMPLES

Example 1

Plastic filaments comprising 1% of the antibiotic tobramycin were prepared with a two-step process as follows. First step: a master batch comprising 10% tobramycin was prepared by dry-mixing together 1 kg of the antibiotic (sourced from Prinova Canada, Scarborough, ON, CA) with 9 kg of PLA granules sourced from Nature Works LLC (Blair, Neb., USA). The 10% master batch was fed into the feed throat of a LEISTRITZ® lab twin-screw extruder (LEISTRITZ is a registered trademark of Leistritz Aktiengesellschaft Stock Corp., Nürnberg, Fed. Rep. Germany), after which, the extruded strands were pelletized. Second step: 1 kg of the 10% tobramycin/PLA pellets were dry-mixed together with 9 kg of PLA granules after which, the dry blend mixture was fed into the feed throat of a DAVIS-STANDARD® single screw extruder (DAVIS-STANDARD is a registered trademark of Davis-Standard LLC, Pawcatuck, Conn., USA), and extruding a mono-filament with a nominal diameter of 0.051 inches+/−0.002 inches. The mono-filament was air cooled after leaving the extruder die to prevent internal filament porosity, characterized using a laser gauging system for diameter and ovality, and then wound onto a High-impact Polystyrene (HIPS) spool with a 6-inch diameter hub. A control filament was prepared by extruding PLA granules into a mono-filament that was cooled and then wound onto a HIPS spool with a 6-inch diameter hub.

The 1% tobramycin PLA filament was supplied to the extrusion nozzle of a STRATASYS® MOJO® FDM® 3D printer (STRATASYS and MOJO are registered trademarks of Stratasys Inc., Eden Prairie, Minn., USA) to print replicate test coupons with an extrusion temperature of 205° C. Each test coupon had a diameter of 25 mm and a thickness of 2.5 mm, and one surface with a "shiny" appearance and the other surface having a "matte" appearance. Control coupons having the same physical dimensions and appearance as the test coupons, were printed with the STRATASYS® MOJO® FDM® 3D primer by feeding the control PLA filament through the extrusion nozzle at an extrusion temperature of 205° C.

Aliquots of a culture of Staphylococcus aureus grown in Tryptic soy broth (TSB) were plated onto the surface of Tryptic soy agar (TSA) contained within Petri plates. Two test coupons were placed onto the plated S. aureus culture in a Petri plate with one shiny side down and one matte side down. Two control coupons were placed onto the plated S. aureus culture in a Petri plate with one shiny side down and one matte side down. Triplicate plates were prepared with test coupon and with control coupons. The Petri plates were incubated for 72 h at 37° C. after which, the plates were examined for the occurrence of zones of inhibition around the coupons. No inhibition of the growth of S. aureus in the Petri plates receiving the control coupons. However, significant zones of inhibition in the growth of S. aureus were observed around the shiny surfaces (37.7 mm) and the matte surfaces (36.3 mm) of the test coupons thereby confirming that tobramycin was eluted from the 3D-printed articles comprising 1% of this antibiotic in PLA.

Example 2

Four different types of antibiotic-containing plastic filaments were prepared with three different concentrations (1% w/w; 2% w/w; 5% w/w) of three antibiotics, i.e., tobramycin, and gentamicin, vancomycin, for use in 3D printing by FDM® machines. The four plastics tested were: (i) polylactic acid (PLA), (ii) polycaprolactone (PCL), (iii) high-density polyethylene (HDPE), and (v) nylon 12 (N12). Those skilled in these arts will know that articles produced with PLA and PCL are resorbable, i.e., they are materials that are broken down and assimilated by a mammalian body over an extended time-period. The skilled person will also know that articles produced with HDPE and N12 are non-resorbable, i.e., they are materials that will not break down and be assimilated by a mammalian body over extended time periods. The different combinations of antibiotics and polymers produced for this example are shown in Table 1.

Tobramycin was sourced from Prinova Canada. Gentamicin and vancomycin were sourced from Gold Biotechnology Inc. (St. Louis, Mo. USA). PLA granules were sourced from NatureWorks LLC. PCL granules were sourced from Perstorp Plastics Systems Inc. (Lakewood, Wash., USA). HDPE granules were sourced from A. Schulman Americas (Akron, Ohio, USA). Nylon 12 granules were sourced from EMS-Chemie (North America) Inc. (Sumter, S.C., USA). A 10% master batch of each antibiotic polymer mixture was prepared as outlined in Example 1. Subsequently, the 1%, 2%, and 5% antibiotic polymer mixtures were prepared as outlined in Example 1 with the appropriate quantities of the 10% antibiotic master blend mixed with pure polymer granules to arrive at the target mixtures after which, each target mixture was fed into the feed throat of a DAVIS-STANDARD® single screw extruder for extrusion of a mono-filament. The individual mono-filaments were air cooled after leaving the extruder die to prevent internal filament porosity, characterized using a laser gauging system for diameter and ovality, and then wound onto High-impact Polystyrene (HIPS) spools with 6-inch diameter hubs.

TABLE 1

Antibiotic-containing plastic filaments produced for 3D printing

| Antibiotic | AB %[1] | PLA[2] | PCL[3] | HDPE[4] | N12[5] |
|---|---|---|---|---|---|
| Tobramycin | 0 | Yes | —[6] | Yes | — |
|  | 1 | Yes | — | Yes | — |
|  | 2 | Yes | — | Yes | — |
|  | 5 | Yes | — | Yes | — |
| Gentamicin | 0 | Yes | Yes | — | Yes |
|  | 1 | Yes | Yes | — | Yes |
|  | 2 | Yes | Yes | — | Yes |
|  | 5 | Yes | Yes | — | Yes |
| Vancomycin | 0 | Yes | Yes | — | Yes |
|  | 1 | Yes | Yes | — | Yes |
|  | 2 | Yes | Yes | — | Yes |
|  | 5 | Yes | Yes | — | Yes |

[1] AB % = % antibiotic in plastic filament w/w
[2] PLA = polylactic acid
[3] PCL = polycaprolactone
[4] HDPE = high-density polyethylene
[5] N12 = nylon 12
[6] — = not done Selected physical properties of the antibiotic-containing plastic filaments were determined following the test methods set out in ASTM D636 document titled "Standard Test Method for Tensile Properties of Plastics" published by ASTM International and publicly available from their website: http://www.astm.org/Standards/D638.htm. The physical properties of the antibiotic-containing plastic filaments are listed in Tables 2-9.

TABLE 2

Physical properties of PLA filaments containing tobramycin

| | Tobramycin content in PLA filaments* | | | |
|---|---|---|---|---|
| Physical parameter | 0 | 1% | 2% | 5% |
| Diameter (inches) | 0.071 | 0.035 | 0.05 | 0.05 |
| Peak load (lbf) | 13.4 ± 0.2 | 8.4 ± 0.6 | 11.5 ± 0.4 | 5.1 ± 1.5 |
| Peak stress (lbf/in$^2$) | 3393.9 ± 61.1 | 8731.5 ± 655.8 | 5853.1 ± 191.2 | 2579.6 ± 758.7 |

TABLE 2-continued

Physical properties of PLA filaments containing tobramycin

| Physical parameter | Tobramycin content in PLA filaments* | | | |
|---|---|---|---|---|
| | 0 | 1% | 2% | 5% |
| Strain at break (%) | 1.68 ± 0.05 | 1.34 ± 0.06 | 0.91 ± 0.14 | 0.48 ± 0.25 |
| Modulus (lbf/in$^2$) | 419148.4 ± 42180.8 | 611923.6 ± 33989.1 | 628082.5 ± 194179.6 | 635066.5 ± 214856.0 |

*data are means of three replicates ± SD

TABLE 3

Physical properties of PLA filaments containing gentamicin

| Physical parameter | Gentamicin content in PLA filaments* | | | |
|---|---|---|---|---|
| | 0 | 1% | 2% | 5% |
| Diameter (inches) | 0.071 | 0.05 | 0.05 | 0.05 |
| Peak load (lbf) | 13.4 ± 0.2 | 10.9 ± 0.5 | 11.4 ± 0.2 | 11.4 ± 0.2 |
| Peak stress (lbf/in$^2$) | 3393.9 ± 61.1 | 5531.1 ± 269.5 | 5778.6 ± 113.5 | 6336.1 ± 102.3 |
| Strain at break (%) | 1.68 ± 0.05 | 1.06 ± 0.22 | 1.09 ± 0.06 | 1.17 ± 0.06 |
| Modulus (lbf/in$^2$) | 419148.4 ± 42180.8 | 604840 ± 244516.8 | 450303.6 ± 38473.7 | 546278.1 ± 50610.4 |

*data are means of three replicates ± SD

TABLE 4

Physical properties of PLA filaments containing vancomycin

| Physical parameter | Vancomycin content in PLA filaments* | | | |
|---|---|---|---|---|
| | 0 | 1% | 2% | 5% |
| Diameter (inches) | 0.071 | 0.05 | 0.05 | 0.05 |
| Peak load (lbf) | 13.4 ± 0.2 | 13.0 ± 0.7 | 12.4 ± 1.8 | 13.1 ± 0.8 |
| Peak stress (lbf/in$^2$) | 3393.9 ± 61.1 | 6609.7 ± 332.2 | 6290.1 ± 908.2 | 6653.3 ± 391.2 |
| Strain at break (%) | 1.68 ± 0.05 | 0.98 ± 0.11 | 1.19 ± 0.65 | 1.41 ± 0.27 |
| Modulus (lbf/in$^2$) | 419148.4 ± 42180.8 | 671627.6 ± 145252.7 | 1038602.0 ± 395613.8 | 522213.5 ± 35208.2 |

*data are means of three replicates ± SD

TABLE 5

Physical properties of PCL filaments containing gentamicin

| Physical parameter | Gentamicin content in PCL filaments* | | | |
|---|---|---|---|---|
| | 0 | 1% | 2% | 5% |
| Diameter (inches) | 0.05 | 0.05 | 0.05 | 0.05 |
| Peak load (lbf) | 3.7 ± 0.2 | 3.7 ± 0.2 | 3.8 ± 0.2 | 3.7 ± 0.2 |
| Peak stress (lbf/in$^2$) | 1912.5 ± 49.8 | 1879.2 ± 99.7 | 2113.1 ± 102.9 | 1861.3 ± 69.1 |
| Modulus (lbf/in$^2$) | 55555.9 ± 1517.8 | 604840 ± 244516.8 | 58610.4 ± 2657.2 | 57471.36 ± 2302.3 |

*data are means of three replicates ± SD

TABLE 6

Physical properties of PCL filaments containing vancomycin

| Physical parameter | Vancomycin content in PCL filaments* | | | |
|---|---|---|---|---|
| | 0 | 1% | 2% | 5% |
| Diameter (inches) | 0.05 | 0.05 | 0.05 | 0.05 |
| Peak load (lbf) | 3.7 ± 0.2 | 3.7 ± 0.2 | 3.6 ± 0.02 | 3.5 ± 0.1 |
| Peak stress (lbf/in$^2$) | 1912.5 ± 49.8 | 1937.3 ± 47.5 | 1825.8 ± 108.7 | 1789.2 ± 53.0 |
| Modulus (lbf/in$^2$) | 55555.9 ± 1517.8 | 51031.2 ± 1086.2 | 50216.9 ± 424.2 | 51517.0 ± 3950.4 |

*data are means of three replicates ± SD

TABLE 7

Physical properties of HDPE filaments containing tobramycin

| | Tobramycin content in HDPE filaments* | | | |
|---|---|---|---|---|
| Physical parameter | 0 | 1% | 2% | 5% |
| Diameter (inches) | 0.05 | 0.05 | 0.05 | 0.05 |
| Peak load (lbf) | 3.8 ± 0.1 | 4.1 ± 0.1 | 4.2 ± 0.1 | 4.1 ± 0.1 |
| Peak stress (lbf/in$^2$) | 1938.6 ± 38.1 | 2098.6 ± 45.3 | 2160.3 ± 32.3 | 2051.4 ± 28.2 |
| Modulus (lbf/in$^2$) | 77164.13 ± 2407.7 | 88987.4 ± 3410.3 | 90373.6 ± 1156.1 | 99006.4 ± 7086+2 |

*data are means of three replicates ± SD

TABLE 8

Physical properties of N12 filaments containing gentamicin

| | Gentamicin content in N12 filaments* | | | |
|---|---|---|---|---|
| Physical parameter | 0 | 1% | 2% | 5% |
| Diameter (inches) | 0.05 | 0.05 | 0.05 | 0.05 |
| Peak load (lbf) | 10.9 ± 0.2 | 10.9 ± 0.1 | 10.6 ± 0.1 | 10.8 ± 0.8 |
| Peak stress (lbf/in$^2$) | 5543.5 ± 83.3 | 5552.6 ± 65.9 | 5383.7+54.4 | 5500.5 ± 396.1 |
| Modulus (lbf/in$^2$) | 191838.5 ± 6330.7 | 197138.9 ± 1785.7 | 198748.8 ± 8950.8 | 207710.2 ± 7946.3 |

*data are means of three replicates ± SD

TABLE 9

Physical properties of N12 filaments containing vancomycin

| | Vancomycin content in N12 filaments* | | | |
|---|---|---|---|---|
| Physical parameter | 0 | 1% | 2% | 5% |
| Diameter (inches) | 0.05 | 0.05 | 0.05 | 0.05 |
| Peak load (lbf) | 10.9 ± 0.2 | 10.9 ± 0.1 | 10.3 ± 0.5 | 10.7 ± 0.1 |
| Peak stress (lbf/in$^2$) | 5543.5 ± 83.3 | 5344.4 ± 66.8 | 5246.3 ± 262.2 | 5443.5 ± 61.3 |
| Modulus (lbf/in$^2$) | 191838.5 ± 6330.7 | 195980.7 ± 5111.5 | 201682.2 ± 1576.0 | 212733.5 ± 7729.7 |

*data are means of three replicates ± SD

Each antibiotic-containing filament was separately supplied to the extrusion nozzle of a STRATASYS® MOJO® FDM® 3D printer to print replicate test coupons, each coupon having the physical dimensions of a diameter of 25 mm and a thickness of 2.5 mm, with one surface having a "shiny" appearance and the other surface having a "matte" appearance. Control coupons having the same physical dimensions and appearance as the test coupons, were printed with the STRATASYS® MOJO® printer by feeding the control filaments through the extrusion nozzle. The 2% and 5% tobramycin/PLA test coupons were printed with an extrusion temperature of 170° C., while the PLA control coupons and the 1% tobramycin PLA test coupons were printed with an extrusion temperature of 205° C. The N12 control coupons, the 1%, 2% and 5% gentamicin/N12 coupons, and the 1%, 2%, and 5% vancomycin/N12 coupons were printed at an extrusion temperature of 195° C. The remaining control coupons and test coupons were printed with an extrusion temperature of 170° C.

Example 3

The elution of antibiotics from the test coupons produced in Example 2 was assessed by the inhibition of the growth of S. aureus on the surfaces of Meuller Hinton agar contained within Petri dishes onto which test coupons placed. S. aureus cultures were grown on TSA amended with 5% sheep blood. A sufficient amount of S. aureus culture was transferred from the TSA culture plates to a 0.85% sterile saline solution to provide a uniform suspension that fell within a 0.5-2.0 McFarland turbidity standard. Aliquots of the S. aureus culture were plated onto Meuller Hinton agar in Petri dishes after which, two test coupons/dish (or alternatively, control coupons) were placed on the agar; one with its shiny side up and the other with its matte side up. The Meuller Hinton agar-containing Petri dishes were then incubated for about 72 hrs at temperatures in the range of about 35° C. to about 37° C. The zones of inhibition around each coupon were then measured and recorded (in mm). A clear zone around a test coupon indicates the inhibition of growth of S. aureus. The diameter of a control coupon is 25 mm and is considered the "0" point. If no inhibition occurred, then the value "25" was recorded and indicates that no inhibition of microbial growth occurred. The data shown in Tables 10, 11, and 12 confirm that all three antibiotics tested, i.e., tobramycin, gentamicin, and vancomycin, were eluted from articles printed with extruded antibiotic-containing polymers as evidenced by zones of inhibition of S. aureus cultures by articles comprising PLA polymer (Table 10), inhibition of S. aureus cultures by articles comprising PCL polymer (Table 11), and inhibition of S. aureus cultures by articles comprising HPDE polymer (Table 12).

TABLE 10

Elution of antibiotics from 3D-printed articles comprising PLA

| Antibiotic | Antibiotic concentration | | | |
|---|---|---|---|---|
| | Control | 1% | 2% | 5% |
| Tobramycin | 25 | 37.7 | 27.5 | 28 |
| Gentamicin | 25 | 34.0 | 26.5 | 37.5 |

TABLE 12

Elution of antibiotics from 3D-printed articles comprising HDPE polymer

| Antibiotic | Antibiotic concentration | | | |
|---|---|---|---|---|
| | Control | 1% | 2% | 5% |
| Tobramycin | 25 | 27.0 | 28.5 | 37.5 |

TABLE 11

Elution of antibiotics from 3D-printed articles comprising PCL polymer

| Antibiotic | Antibiotic concentration | | | |
|---|---|---|---|---|
| | Control | 1% | 2% | 5% |
| Gentamicin | 25 | 32.0 | 38.5 | 41.0 |
| Vancomycin | 25 | 28.5 | 25 | 28.5 |

Example 4

A study was done to assess the 3D printing performance of a polymer loaded with a combination of three antibiotics (tobramycin, gentamicin, vancomycin) and the elution of the antibiotics from 3D printed articles comprising the antibiotic-loaded polymer. A 10% master batch of each antibiotic dry-mixed with PLA was prepared, then extruded with a LEISTRITZ® lab twin-screw extruder after which, the extruded strands were pelletized. Then, 1 kg of each master batch was dry-mixed with 7 kg of PLA granules after which, the dry blend mixture was fed into the feed throat of a DAVIS-STANDARD® single screw extruder from which was extruded a mono-filament that comprised 3% antibiotics (i.e., 1% tobramycin+1% gentamicin+1% vancomycin). The mono-filament was air-cooled after leaving the extruder die to prevent internal filament porosity, characterized using a laser gauging system for diameter and ovality, and then wound onto a High-impact Polystyrene (HIPS) spool with a 6-inch diameter hub. A control filament was prepared by extruding PLA granules into a mono-filament that was cooled and then wound onto a HIPS with a 6-inch diameter hub.

Selected physical properties of the three antibiotic-containing plastic mono-filaments were determined following the test methods as described in Example 2. The physical properties of the three antibiotic-containing plastic mono-filaments are listed in Table 13.

TABLE 13

| Physical parameter | Antibiotic concentration | |
|---|---|---|
| | 0 | 3% |
| Diameter (inches) | 0.07 | 0.05 |
| Peak load (lbf) | 13.4 ± 0.2 | 11.7 ± 0.4 |
| Peak stress (lbf/in$^2$) | 3393.9 ± 61.1 | 5948.2 ± 0.4 |
| Strain at break (%) | 1.68 ± 0.05 | 1.03 ± 0.08 |
| Modulus (lbf/in$^2$) | 419148.4 ± 42180.8 | 550481.3 ± 45529.63 |

The three-antibiotic-containing filament was supplied to the extrusion nozzle of a STRATASYS® MOJO® FDM® 3D printer to print replicate test coupons at an extrusion temperature of 170° C., each coupon having the physical dimensions of a diameter of 25 mm and a thickness of 2.5 mm, with one surface having a "shiny" appearance and the other surface having a "matte" appearance. The control coupons for this study were taken from the batch of control coupons produced in Example 1.

The elution of antibiotics from the test coupons comprising 3% of the combined three antibiotics in PLA, was assessed by the inhibition of the growth of *S. aureus* on the surfaces of Meuller Hinton agar as described in Example 3. The data shown in Table 14 confirm that the three antibiotics were eluted from articles printed with extruded polymers comprising the three antibiotics.

TABLE 14

| Antibiotic | Antibiotic concentration | |
|---|---|---|
| | 0 | 3% |
| 1% tobramycin + 1% gentamicin + 1% vancomycin | 25 | 36.5 |

The invention claimed is:

1. An antibiotic-eluting article comprising an antibiotic-containing polymeric mono-filament consisting of:
    a dry blend of: a polymer and at least one antibiotic;
    wherein the amount of the at least one antibiotic is between about 0.1 weight percent and about 20.0 weight percent relative to the total weight of the antibiotic-containing polymeric mono-filament;
    wherein the polymer is selected from the group consisting of: polylactic acid, polycaprolactone, polyamide, and polyethylene;
    wherein the diameter of the antibiotic-containing polymeric mono-filament is in the range of about 0.89 millimeters to about 3.0 millimeters,
    wherein the polymer and the at least one antibiotic are homogenously distributed throughout the antibiotic-containing polymeric mono-filament,
    wherein the dry blend has been extruded through an extrusion die to produce the antibiotic-containing polymeric mono-filament, and
    wherein the antibiotic-containing polymeric mono-filament is extrudable through a fused deposition modelling machine to produce the antibiotic-eluting article having the at least one antibiotic homogenously distributed throughout and elutable from the antibiotic-eluting article.

2. The antibiotic-eluting article of claim 1, wherein the antibiotic is selected from the group consisting of an aminoglycoside, an azole, a β-lactam antibiotic, a β-lactamase inhibitor, a cephalosporin, chloramphenicol, clindamycin, fusidic acid, a glycopeptide, a macrolide, metronidazole, mupirocin, a penicillin, a polyene, a quinolone, a rifamycin, a sulfonamide, tetracycline, trimethoprim, and combinations thereof.

3. The antibiotic-eluting article of claim 1, wherein the amount of the at least one antibiotic is between about 0.5 weight percent and about 10.0 weight percent relative to the total weight of the antibiotic-containing polymeric mono-filament.

4. The antibiotic-eluting article of claim 1, wherein the amount of the at least one antibiotic is between about 0.75 weight percent and about 5.0 weight percent relative to the total weight of the antibiotic-containing polymeric mono-filament.

5. An antibiotic-eluting article comprising an antibiotic-containing polymeric mono-filament consisting of:
    a dry blend of: a polymer, at least one antibiotic, and a bone-growth-promoting composition;
    wherein the amount of the at least one antibiotic is between about 0.1 weight percent and about 20.0 weight percent relative to the total weight of the antibiotic-containing polymeric mono-filament;
    wherein the polymer is selected from the group consisting of: polylactic acid, polycaprolactone, polyamide, and polyethylene;
    wherein the diameter of the antibiotic-containing polymeric mono-filament is in the range of about 0.89 millimeters to about 3.0 millimeters,
    wherein the polymer and the at least one antibiotic are homogenously distributed throughout the antibiotic-containing polymeric mono-filament,
    wherein the dry blend has been extruded through an extrusion die to produce the antibiotic-containing polymeric mono-filament, and
    wherein the antibiotic-containing polymeric mono-filament is extrudable through a fused deposition modelling machine to produce the antibiotic-eluting article having the at least one antibiotic homogenously distributed throughout and elutable from the antibiotic-eluting article.

6. The antibiotic-eluting article of claim 5, wherein the bone-growth-promoting composition is selected from the group consisting of: hyaluronic acid, β-(tricalcium phosphate), SOST (sclerostin), an antagonist that modulates the Wnt signaling pathway, (3-((4(4-tert-butyl-benzyl)-(pyridine-3-sulfonyl)-amino)-methyl)-phenoxy-)-acetic-acid and its analogs, 7-[(4-butyl-benzyl)-methanesulfonyl-amino] heptanoic acid and its analogs, 7-{[2-(3,5-dichloro-phenoxyl)-ethyl]-methanesulfonyl-amino}-heptanoic acid and its analogs, and 3-benzothiepin derivatives.

7. The antibiotic-eluting article of claim 1, wherein the antibiotic composition is selected from the group consisting of tobramycin, gentamicin, vancomycin, and combinations thereof.

8. The antibiotic-eluting article of claim 1, wherein the antibiotic-eluting article is provided with an outer coat comprising a biocidal composition.

9. The antibiotic-eluting article of claim 8, wherein the outer coat comprises one or more of silver nanoparticles, zinc pyrithione, and cationic polymeric biocides.

10. The antibiotic-eluting article of claim 1, wherein the article is an orthopaedic skeletal component.

11. The antibiotic-eluting article of claim 1, wherein the article is an orthopaedic articulating joint replacement component.

12. The antibiotic-eluting article of claim 1, wherein the article is an external casing for an implantable device.

13. The antibiotic-eluting article of claim 1, wherein the article is selected from the group consisting of a cardiac pacemaker, a spinal cord stimulator, a neurostimulation system, an intrathecal drug pump for delivery of medicants into the spinal fluid, an infusion pump for delivery of chemotherapeutics and/or anti-spasmodics, an insulin pump, an osmotic pump, and a heparin pump.

14. The antibiotic-eluting article of claim 1, wherein the article is an implantable dental prosthesis or a replacement tooth component.

15. The antibiotic-eluting article of claim 1, wherein the article is a transcutaneous skin surface treatment device.

16. The antibiotic-eluting article of claim 1, wherein the article is a wound treatment device.

* * * * *